United States Patent
Daly et al.

(10) Patent No.: US 7,421,298 B2
(45) Date of Patent: Sep. 2, 2008

(54) MULTIPLE CHANNEL-ELECTRODE MAPPING

(75) Inventors: Christopher Daly, Bilgola Plateau (AU); Peter Seligman, Essendon (AU); Kerrie Plant, Cheltenham (AU); Mary-Ann Law, East Melbourne (AU)

(73) Assignee: Cochlear Limited (AU)

(*) Notice: Subject to any disclaimer, the term of this patent is extended or adjusted under 35 U.S.C. 154(b) by 331 days.

(21) Appl. No.: 11/219,823

(22) Filed: Sep. 7, 2005

(65) Prior Publication Data

US 2006/0052841 A1 Mar. 9, 2006

Related U.S. Application Data

(63) Continuation-in-part of application No. 11/192,014, filed on Jul. 29, 2005.

(60) Provisional application No. 60/607,363, filed on Sep. 7, 2004.

(51) Int. Cl.
*A61N 1/36* (2006.01)
(52) U.S. Cl. ....................................................... 607/57
(58) Field of Classification Search .................. 607/57, 607/56, 55, 2
See application file for complete search history.

(56) References Cited

U.S. PATENT DOCUMENTS

| 4,532,930 | A | 8/1985 | Crosby et al. |
| 4,617,913 | A * | 10/1986 | Eddington ................ 607/57 |
| 5,271,397 | A | 12/1993 | Seligman et al. |
| 6,537,200 | B2 | 3/2003 | Leysieffer et al. |
| 6,565,503 | B2 | 5/2003 | Leysieffer et al. |
| 6,575,894 | B2 | 6/2003 | Leysieffer et al. |
| 6,697,674 | B2 | 2/2004 | Leysieffer et al. |

FOREIGN PATENT DOCUMENTS

WO 02/17679 2/2002

* cited by examiner

*Primary Examiner*—Kennedy J Schaetzle
(74) *Attorney, Agent, or Firm*—Connolly Bove Lodge & Hutz

(57) ABSTRACT

In accordance with one aspect of the invention, methods and systems are disclosed for delivering a stimulating signal by a stimulating medical device having a plurality of electrodes. Such methods and systems comprise receiving a signal; filtering the received signal to obtain a plurality of band pass filtered signals; delivering to each electrode of a first group of one or more electrodes, a first set of stimulation signals, wherein the first set of stimulation signals comprises stimulations signals for each of a first group of two or more band pass filtered signals; and delivering to each of electrodes of a second group of one or more electrodes, a second set of stimulation signals, wherein the second set of stimulation signals comprises stimulations signals for each of a second group of one or more band pass filtered signals; and wherein the first set of stimulation signals are delivered at a different effective stimulation rate than the second set of stimulation signals.

18 Claims, 11 Drawing Sheets

FIG. 5

| CHANNEL GROUP | E | STIMULUS TIMING SEQUENCE ||||||||||||||
| --- | --- | --- | --- | --- | --- | --- | --- | --- | --- | --- | --- | --- | --- | --- | --- |
| | | T1 | T2 | T3 | T4 | T5 | T6 | T7 | T8 | T9 | T10 | T11 | T12 | T13 | T14 |
| 8 (CHANNELS 2,3,4) | 4 | X | X | X | | | | | | | | | | | |
| 7 (CHANNELS 8,7,6) | 7 | | | | X | X | X | | | | | | | | |
| 6 (CHANNELS 10,11) | 10 | | | | | | | X | X | | | | | | |
| 5 (CHANNELS 13,14) | 14 | | | | | | | | | X | X | | | | |
| 4 (CHANNEL 16) | 16 | | | | | | | | | | | X | | | |
| 3 (CHANNEL 18) | 18 | | | | | | | | | | | | X | | |
| 2 (CHANNEL 20) | 20 | | | | | | | | | | | | | X | |
| 1 (CHANNEL 22) | 22 | | | | | | | | | | | | | | X |

FIG. 6

| CHANNEL GROUP | E | STIMULUS TIMING SEQUENCE ||||||||||||||
| --- | --- | --- | --- | --- | --- | --- | --- | --- | --- | --- | --- | --- | --- | --- | --- |
| | | T1 | T2 | T3 | T4 | T5 | T6 | T7 | T8 | T9 | T10 | T11 | T12 | T13 | T14 |
| 8 (CHANNELS 2,3,4) | 4 | X | | | | | X | | | | | X | | | |
| 7 (CHANNELS 8,7,6) | 7 | | X | | | | | X | | | | | X | | |
| 6 (CHANNELS 10,11) | 10 | | | X | | | | | X | | | | | | |
| 5 (CHANNELS 13,14) | 14 | | | | X | | | | | X | | | | | |
| 4 (CHANNEL 16) | 16 | | | | | X | | | | | | | | | |
| 3 (CHANNEL 18) | 18 | | | | | | | | | | X | | | | |
| 2 (CHANNEL 20) | 20 | | | | | | | | | | | | | X | |
| 1 (CHANNEL 22) | 22 | | | | | | | | | | | | | | X |

FIG. 10

| FILTER CHANNEL NUMBER | USED/UNUSED (1/0) | ELECTRODE NUMBER | ACTIVE/INACTIVE (1/0) |
|---|---|---|---|
| 22 | 1 | 22 | 1 |
| 21 | 1 | 21 | 1 |
| 20 | 1 | 20 | 1 |
| 19 | 1 | 19 | 0 |
| 18 | 1 | 18 | 1 |
| 17 | 1 | 17 | 0 |
| 16 | 1 | 16 | 1 |
| 15 | 1 | 15 | 0 |
| 14 | 1 | 14 | 1 |
| 13 | 1 | 13 | 0 |
| 12 | 1 | 12 | 1 |
| 11 | 1 | 11 | 0 |
| 10 | 0 | 10 | 1 |
| 9 | 0 | 9 | 0 |
| 8 | 0 | 8 | 1 |
| 7 | 0 | 7 | 0 |
| 6 | 0 | 6 | 1 |
| 5 | 0 | 5 | 0 |
| 4 | 0 | 4 | 1 |
| 3 | 0 | 3 | 0 |
| 2 | 0 | 2 | 1 |
| 1 | 0 | 1 | 0 |

FIG. 11

| FILTER CHANNEL NUMBER 1002 | USED/UNUSED (1/0) 1004 | ELECTRODE NUMBER 1006 | ACTIVE/INACTIVE (1/0) 1008 |
|---|---|---|---|
| 22 | 1 | 22 | 1 |
| 21 | 1 | 21 | 1010  0 |
| 20 | 1 | 20 | 1 |
| 19 | 1 | 19 | 1010  0 |
| 18 | 1 | 18 | 1 |
| 17 | 1112  1 | 17 | 1010  0 |
| 16 | 1 | 16 | 1 |
| 15 | 1112  1 | 15 | 1010  0 |
| 14 | 1 | 14 | 1 |
| 13 | 1112  1 | 13 | 1010  0 |
| 12 | 1 | 12 | 0 |
| 11 | 1 | 11 | 0 |
| 10 | 0 | 10 | 1010  1 |
| 9 | 0 | 9 | 0 |
| 8 | 0 | 8 | 0 |
| 7 | 0 | 7 | 1010  1 |
| 6 | 0 | 6 | 0 |
| 5 | 0 | 5 | 0 |
| 4 | 0 | 4 | 1010  1 |
| 3 | 0 | 3 | 0 |
| 2 | 0 | 2 | 0 |
| 1 | 0 | 1 | 0 |

| GROUP NUMBER | FILTER CHANNEL NUMBER | ACTIVE ELECTRODE(S) |
|---|---|---|
| 1 | 22 | 20, 21, 22 |
| 2 | 19 | 18, 19 |
| 3 | 15 | 15, 16, 17 |
| 4 | 14 | 12, 13 |
| 5 | 13 | 12, 13 |
| 5 | 12 | 12, 13 |
| 6 | 11 | 10 |
| 6 | 10 | 10 |
| 7 | 8 | 7 |
| 7 | 7 | 7 |
| 7 | 6 | 7 |
| 8 | 4 | 3, 4 |
| 8 | 3 | 3, 4 |
| 8 | 2 | 3, 4 |

MULTIPLE CHANNEL-ELECTRODE MAPPING

CROSS-REFERENCE TO RELATED APPLICATIONS

This application is a continuation-in-part of U.S. patent application Ser. No. 11/192,014, entitled "Variable Width Electrode Scheme," filed Jul. 29, 2005. This application also claims the benefit of U.S. Provisional Application No. 60/607,363, filed Sep. 7, 2004. The entire disclosure and contents of the above applications are hereby incorporated by reference.

BACKGROUND

1. Field of the Invention

The present invention relates generally to a stimulating medical device and, more particularly, to multi-channel stimulation of a medical device.

2. Related Art

Delivery of electrical stimulation to appropriate locations within a recipient or patient (referred to herein as a recipient) may be used for a variety of purposes. For example, function electrical stimulation (FES) systems may be used to deliver electrical pulses to certain muscles of a recipient to cause a controlled movement of a limb of the recipient.

As another example, a prosthetic hearing implant system may be used to directly deliver electrical stimulation to auditory nerve fibers of a recipient's cochlea to cause the recipient's brain to perceive a hearing sensation resembling the natural hearing sensation normally delivered to the auditory nerve.

Prosthetic hearing implant systems typically have two primary components: an external component commonly referred to as a speech processor, and an implanted component commonly referred to as a receiver/stimulator unit. Traditionally, both of these components cooperate with each other to provide sound sensations to a recipient.

The external component traditionally includes a microphone that detects sounds, such as speech and environmental sounds, a speech processor that selects and converts certain detected sounds, particularly speech, into a coded signal, a power source such as a battery, and an external transmitter antenna.

The coded signal output by the speech processor is transmitted transcutaneously to the implanted receiver/stimulator unit, commonly located within a recess of the temporal bone of the recipient. This transcutaneous transmission occurs via the external transmitter antenna which is positioned to communicate with an implanted receiver antenna disposed within the receiver/stimulator unit. This communication transmits the coded sound signal while also providing power to the implanted receiver/stimulator unit. Conventionally, this link has been in the form of a radio frequency (RF) link, but other communication and power links have been proposed and implemented with varying degrees of success.

The implanted receiver/stimulator unit traditionally includes the noted receiver antenna that receives the coded signal and power from the external component. The implanted unit also includes a stimulator that processes the coded signal and outputs an electrical stimulation signal to an intra-cochlea electrode assembly mounted to a carrier member. The electrode assembly typically has a plurality of electrodes that apply the electrical stimulation directly to the auditory nerve to produce a hearing sensation corresponding to the original detected sound.

In the conversion of sound to electrical stimulation by the speech processor, it is common in the prosthetic hearing implant field to allocate frequencies from a filter bank or similar frequency analyzer to individual electrodes of the electrode assembly. This "mapping" is typically done on a one-to-one basis, that is, each filter output is allocated to a single electrode. It is typical to allocate frequencies to electrodes that lie in positions in the cochlea that are close to the region that would naturally be stimulated in normal hearing. However, signal processing techniques implemented in conventional prosthetic hearing devices often fail to map to the optimal electrodes in the cochlea, thus limiting their ability to provide the desired perception of hearing.

SUMMARY

According to one aspect of the invention, methods and systems are provided for delivering a stimulating signal by a stimulating medical device having a plurality of electrodes. Such methods and systems comprise receiving a signal; filtering the received signal to obtain a plurality of band pass filtered signals; delivering to each electrode of a first group of one or more electrodes, a first set of stimulation signals, wherein the first set of stimulation signals comprises stimulations signals for each of a first group of two or more band pass filtered signals; and delivering to each of electrodes of a second group of one or more electrodes, a second set of stimulation signals, wherein the second set of stimulation signals comprises stimulations signals for each of a second group of one or more band pass filtered signals; and wherein the first set of stimulation signals are delivered at a different effective stimulation rate than the second set of stimulation signals.

According to another aspect, methods and systems are provided for a cochlear implant system, comprising a plurality of electrodes disposed in a cochlear of a recipient, wherein the plurality of electrodes comprise a first group of one or more electrodes and a second group of one or more electrodes, a speech processor, and a stimulator unit. According to an aspect, the speech processor comprises a plurality of band pass filters configured to process received acoustical signals to obtain a plurality of band pass filtered signals. Further, in an aspect, the stimulator unit is configured to deliver to each electrode of a first group of one or more electrodes, a first set of stimulation signals, wherein the first set of stimulation signals comprises stimulations signals for each of a first group of two or more band pass filtered signals, and to deliver to a second group of one or more electrodes a second set of stimulation signals, wherein the second set of stimulation signals comprises stimulations signals for each of a second group of one or more band pass filtered signals, and wherein the first set of stimulation signals are delivered at a different effective stimulation rate than the second set of stimulation signals.

BRIEF DESCRIPTION OF THE DRAWINGS

FIG. 5 illustrates a table that provides an exemplary stimulus timing sequence for a simple stimulation strategy;

FIG. 6 illustrates a table that provides an alternative channel timing sequence for a stimulation strategy;

FIG. 10 illustrates an exemplary table of a default mapping that provides 12 effective filter channels;

FIG. 11 illustrates an exemplary table of a mapping after modification by an audiologist;

DETAILED DESCRIPTION

The present invention is generally directed to a stimulating medical device comprising a plurality of tissue-stimulating electrodes in which the electrode geometry may be adjusted without replacing or altering the physical arrangement of the electrodes on or implanted in a recipient. An embodiment of the present invention includes a multi-electrode stimulating device that generates stimulation signals based on a multiple-to-one correspondence between filter channels and electrodes. This mapping of multiple filter channels to a single electrode, or a single group of electrically-coupled electrodes, will be referred to as the Multiple Electrode Mapping (MEM) strategy. In contrast to the one-to-one correspondence between filter channels and electrodes in traditional systems, the MEM strategy permits a mapping of two or more filter channels to a single group of one or more electrodes.

The MEM strategy provides many advantages such as, for example, allowing electrodes corresponding to different frequency ranges to be stimulated at different stimulation rates to provide improved speech perception. For example, higher frequency channels may be stimulated at a higher rate to more closely approximate natural hearing. The MEM strategy also allows for combining frequency channels to provide effectively wider frequency channels to individual electrodes, thus reducing the effective number of frequency channels delivered to the electrodes of an electrode array. Further assigning/delivering multiple filter channels to a single electrode (or a single group of electrically-coupled electrodes) that is stimulated at a higher stimulation rate has the effect of increasing the temporal resolution of the system. Thus, combining multiple filter channels may be used to shift a system from a system with a high spectral resolution (i.e., a large number of channels of stimulation) and low temporal resolution (i.e., a lower rate of stimulation) to a system with lower spectral resolution (i.e., less stimulation channels) and higher temporal resolution (i.e., a higher rate of stimulation).

Figure 1:
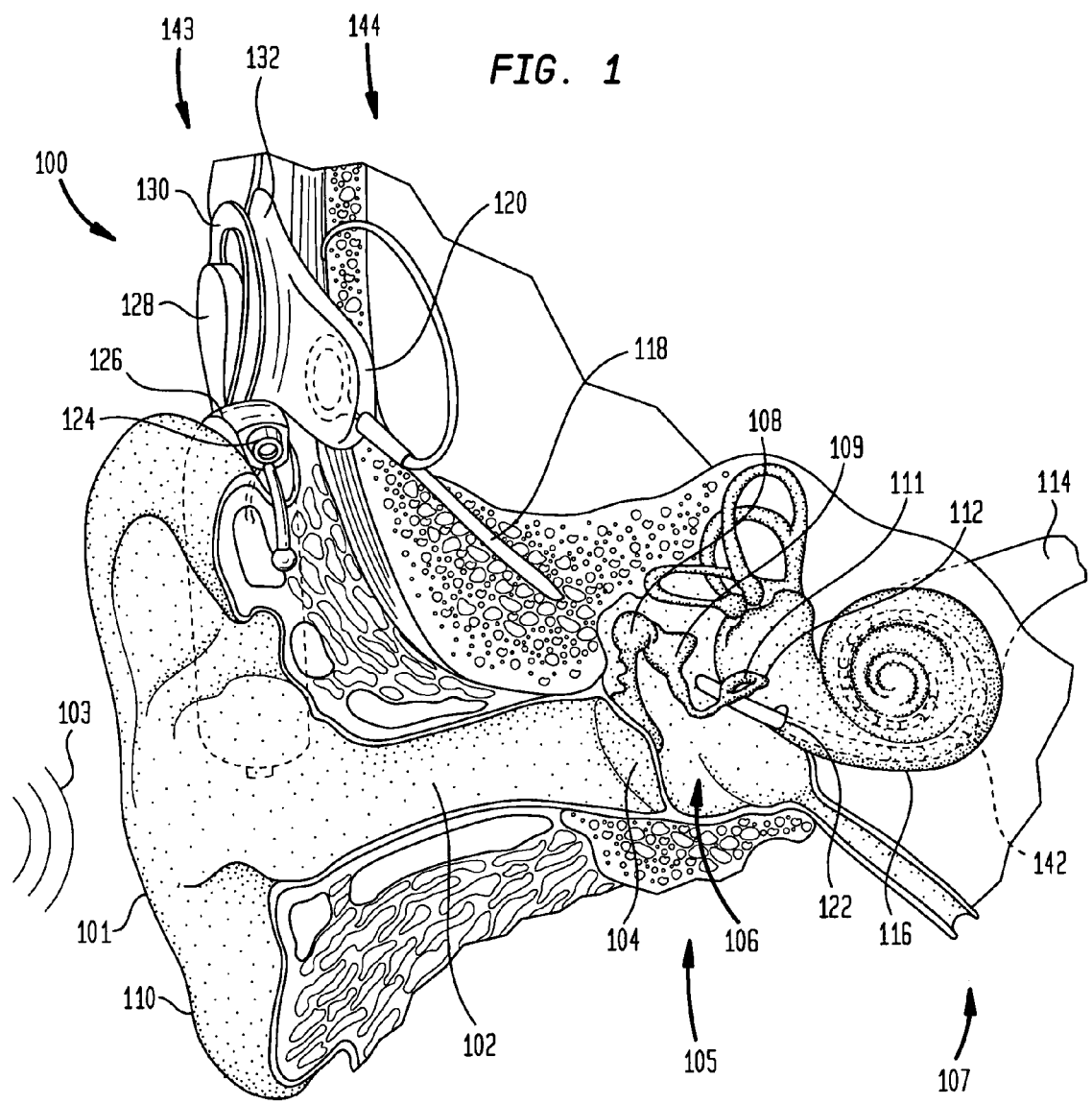
FIG. 1 is a perspective view of an exemplary hearing implant system suitable for implementing embodiments of the present invention.

Embodiments of the present invention are described herein primarily in connection with one type of stimulating medical device, a prosthetic hearing implant system. Prosthetic hearing implant systems include but are not limited to hearing aids, auditory brain stimulators, and Cochlear™ implants (also commonly referred to as Cochlear™ prostheses, Cochlear™ devices, Cochlear™ implant devices, and the like; generally and collectively referred to as "cochlear implants" herein). Cochlear implants use direct electrical stimulation of auditory nerve cells to bypass absent or defective hair cells that normally transduce acoustic vibrations into neural activity. Such devices generally use an electrode array inserted into the scala tympani of the cochlea so that the electrodes may differentially activate auditory neurons that normally encode differential pitches of sound. Auditory brain stimulators are used to treat a smaller number of recipients with bilateral degeneration of the auditory nerve. For such recipients, the auditory brain stimulator provides stimulation of the cochlear nucleus in the brainstem, typically with a planar electrode array; that is, an electrode array in which the electrode contacts are disposed on a two dimensional surface that can be positioned proximal to the brainstem. FIG. 1 is a perspective view of a cochlear implant in which the effective width of the electrodes may be adjusted in accordance with the teachings of the present invention.

FIG. 1 is a perspective view of an exemplary cochlear implant system in which the present invention may be implemented. The relevant components of outer ear 101, middle ear 105 and inner ear 107 are described next below. In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to acoustic wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify acoustic wave 103, causing oval window 112 to articulate, or vibrate. Such vibration sets up waves of fluid motion within cochlea 116. Such fluid motion, in turn, activates tiny hair cells (not shown) that line the inside of cochlea 116. Activation of the hair cells causes appropriate nerve impulses to be transferred through the spiral ganglion cells (not shown) and auditory nerve 114 to the brain (not shown), where they are perceived as sound.

Cochlear implant system 100 comprises external component assembly 143 which is directly or indirectly attached to the body of the recipient, and an internal component assembly 144 which is temporarily or permanently implanted in the recipient. External assembly 143 typically comprises microphone 124 for detecting sound, a speech processing unit 126, a power source (not shown), and an external transmitter unit 128. External transmitter unit 128 comprises an external coil 130 and, preferably, a magnet (not shown) secured directly or indirectly to the external coil. Speech processing unit 126 processes the output of microphone 124 that is positioned, in the depicted embodiment, by ear 110 of the recipient. Speech processing unit 126 generates coded signals, referred to herein as a stimulation data signals, which are provided to external transmitter unit 128 via a cable (not shown). Speech processing unit 126 is, in this illustration, constructed and arranged so that it can fit behind outer ear 110. Alternative versions may be worn on the body or it may be possible to provide a fully implantable system which incorporates the speech processor and/or microphone into the internal component assembly 144.

Internal components 144 comprise an internal receiver unit 132, a stimulator unit 120 and an electrode assembly 118. Internal receiver unit 132 comprises an internal transcutaneous transfer coil (not shown), and preferably, a magnet (also not shown) fixed relative to the internal coil. Internal receiver unit 132 and stimulator unit 120 are hermetically sealed within a biocompatible housing. The internal coil receives power and data from external coil 130, as noted above. A cable or lead of electrode assembly 118 extends from stimulator unit 120 to cochlea 116 and terminates in an array 142 of electrodes. Signals generated by stimulator unit 120 are applied by the electrodes of electrode array 142 to cochlear 116, thereby stimulating the auditory nerve 114.

In one embodiment, external coil 130 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, internal receiver unit 132 may be positioned in a recess of the temporal bone adjacent ear 110 of the recipient.

Further details of the above and other exemplary prosthetic hearing implant systems in which embodiments of the present invention may be implemented include, but are not limited to, those systems described in U.S. Pat. Nos. 4,532,930, 6,537, 200, 6,565,503, 6,575,894 and 6,697,674, which are hereby incorporated by reference herein in their entireties. For example, while cochlear implant system 100 is described as having external components, in alternative embodiments, implant system 100 may be a totally implantable prosthesis. In one exemplary implementation, for example, speech processor 116, including the microphone, speech processor and/or power supply may be implemented as one or more implantable components. In one particular embodiment, speech processor 116 may be contained within the hermetically sealed housing used for stimulator unit 126.

It should also be appreciated that although embodiments of the present invention are described herein in connection with prosthetic hearing device 100, the same or other embodiments of the present invention may be implemented in other tissue-stimulating medical devices as well. Examples of such devices include, but are not limited to, other sensory prosthetic devices, neural prosthetic devices, and functional electrical stimulation (FES) systems. In sensory prostheses, information is collected by electronic sensors and delivered directly to the nervous system by electrical stimulation of pathways in or leading to the parts of the brain that normally process a given sensory modality. Neural prostheses are clinical applications of neural control interfaces whereby information is exchanged between neural and electronic circuits. FES devices are used to directly stimulate tissue having contractile cells to produce a controlled contraction of the same.

It should also be appreciated that although much of the description of the invention is directed to multiple channel-electrode mapping in which adjacent filter channels are grouped and mapped together to stimulate a single group of one or more electrodes, embodiments of the present invention are not limited to grouping adjacent channels, but rather may be used to couple any desired filter channels of a simulating medical device.

Figure 2:
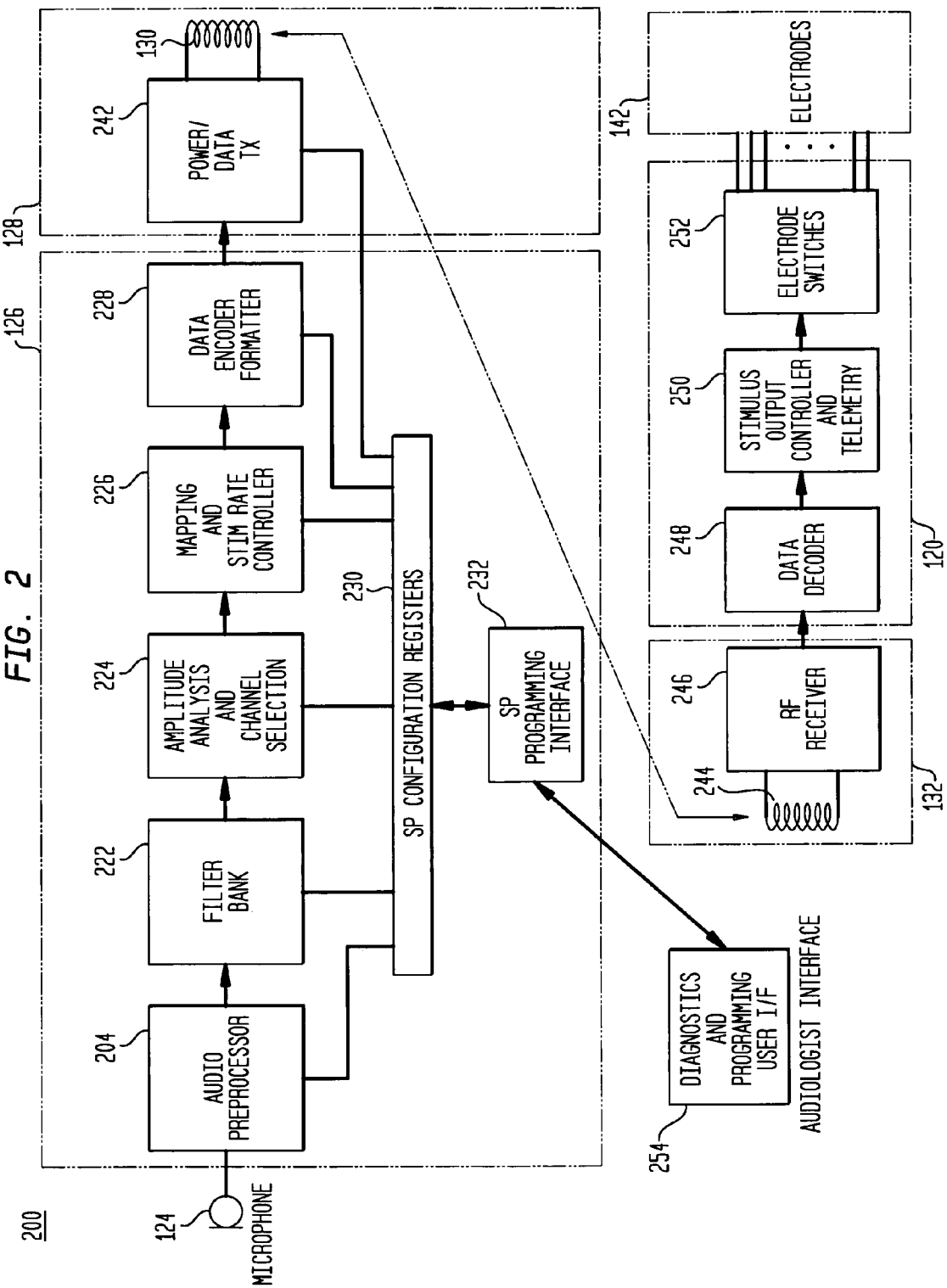
FIG. 2 illustrates a simplified functional block diagram of a hearing implant system in accordance with one embodiment of the present invention.

FIG. 2 is a high-level functional block diagram of one embodiment of a cochlear implant system 100, referred to herein as cochlear implant 200. The functional blocks depicted in FIG. 2 are illustrative only. The functions may be implemented in any combination of hardware, software or combination thereof. The described functions and operations may be combined as depicted in FIG. 2 or may be combined or separated as desired for a particular application.

Cochlear implant 200 comprises one or more microphone (s) 124 as described above with reference to FIG. 1. It should be appreciated, however, that the any audio receiving device now or later developed may be implemented in a prosthetic hearing implant also implementing embodiments of the present invention.

Microphone 124 provides a received audio signal to an audio preprocessor 204. Audio pre-processor 204 may, for example, use a pre-emphasis filter, a pre-amplifier, automatic gain control (AGC), an/or manual sensitivity control (MSC), and other signal pre-processing components. Audio-preprocessor 204 may be implemented, for example, in speech processing unit 126 described above with reference to FIG. 1. The structure and operation of audio-preprocessor 204 is considered to be well-known in the art and, therefore, is not described further herein. Further details of exemplary embodiments of audio-preprocessor 204 may be found in the US patents incorporated by reference elsewhere herein in this application.

Audio pre-processor 204 provides output signals to filter bank 222, which preferably filters the received signals using a bank of band-pass filters 222 to obtain a plurality of frequency channel signals, each corresponding to a particular frequency band. For example, for an implant system providing up to 22 channels of Stimulation, filter bank 222 preferably has 22 separate band pass filters each providing a frequency channel signal corresponding a channel of stimulation. In the presently discussed exemplary embodiments, two different exemplary technologies will be discussed for implementing filter bank 222. The first technology is the Switched Capacitor Filter (SCF) technology that uses a bank of switched capacitory filters (e.g., 22 separate band pass filters). This technology is a power-efficient hardware implementation that enables a behind-the-ear (BTE) speech processor to be built. The filters of the SCF technology can be adjusted (scaled) in frequency by simply changing a clock frequency of an internal clock. The SCF technology is currently implemented in the Spectra™ and ESPrit™ family of speech processors for cochlear implant systems available from Cochlear, Inc. The second technology that will be discussed for implementing filter bank 222 is the Digital Signal Processing (DSP) technology. This technology is implemented in software on a special purpose computer chip using various mathematical algorithms such as the Fast Fourier Transform (FFT). DSP is a flexible technique that can be used to achieve better dynamic range than SCFs, but consumes more power. The DSP technology is currently implemented in the SPrint™ and Freedom™ families of speech processors available from Cochlear, Inc. In systems implementing the DSP technology, the sound signals received by microphone 124 may be converted to digital signals prior to filtering by, for example, an Analog to Digital Converter (ADC) (not shown).

The filter channel signals are provided to an amplitude analysis and channel selection block 224 (hereinafter "ACS block" 224) that optionally selects the maxima that will be used for stimulus application. ACS block 224 may also sample the received filter channel signals to obtain energy estimates (amplitudes) of these signals at times defined by a spectral analysis rate. Maxima selection and obtaining energy estimates of filter channel signals are well known to those of ordinary skill in the art and, as such, are not described further herein. For simplicity, the embodiments described herein will be presented with reference to a Continuous Interleaved Sampling (CIS) system in which maxima are not selected, but instead all filter channels are available for stimulation. A further description of an exemplary ACS block is provided below.

The filter channels signals (or selected maxima of filter channel signals) are then provided to a mapping and stimulation rate controller block 226 (hereinafter "M&SR block" 226) that preferably determines, based on the stimulation strategy being implemented, control information for use in applying stimulus via the electrode array 142, in accordance with the received signals. For example, M&SR block 226 may select, for each of the received filter channel signals (or maxima), the electrode(s) to be used, the timing, the mode of stimulation, and the amplitude of the stimulation to be applied. The selected mode of stimulation may be, for example, bi-polar or mono-polar. In addition, electrodes may be electrically coupled to create electrode groups of one or more electrodes. The electrodes may be grouped, for example, based on a pre-defined strategy for grouping the electrodes (e.g., a strategy based on testing of the implant system after implantation in an implant recipient). Alternatively or additionally, the electrodes may be dynamically grouped based on, for example, characteristics of the received maxima or some combination of both predefined information and dynamic information. Various exemplary strategies for grouping electrodes are described in further detail in related U.S. patent application Ser. No. 11/192,014, entitled "Variable Width Electrode Scheme," filed Jul. 29, 2005.

M&SR block 226 may also map one or more received filter channel signals (or maxima) to a single electrode or a single group of two or more electrodes. M&SR block 226 may map filter channels to electrodes based on a map stored in SP configuration registers 230. This map may, for example, map filter channels to electrodes in a one-to-one correspondence (i.e., a single filter channel is mapped to a single corresponding electrode), or a multi-to-one correspondence (i.e., multiple filter channels are mapped to a single group of one or more electrodes). This map may be modifiable by an audiologist via SP programming interface 232. A further description of mapping multiple filter channels to a single group of one or more electrically-coupled electrodes is provided below.

The electrode information, timing information, mode of stimulation, and the amplitude information may then be provided to a data encoder/formatter 228, which encodes the information for transmission over the trancsutaneous link to internal components 144. A myriad of techniques may be implemented to effect the encoding of information for transmission over the transcutaneous link (see, FIG. 1). These include, but are not limited to, sending information identifying table entries of a table stored in stimulator unit 120, sending the raw information, etc. As one of ordinary skill in the art would appreciate, the implemented encoding technique depends on a variety of factors, including the specific communication technique implemented. The encoded information, in this embodiment, is then provided to a power/data transmitter 242 that transmits the signals using external coil 130. It should be appreciated that any communication technique now or later developed may be implemented in embodiments of the presentation, including, for example, via RF, IR percutaneous lead, etc. It should be appreciated that the structure and function of power/data transmitter 242 will be appropriate for the selected transmission technique.

An internal radio frequency (RF) receiver 246 receives the transmitted information via internal coil 244 and provides it to data encoder 248. Data encoder 248 then decodes the information. As one of ordinary skill in the art would appreciate, the decoding technique is preferably based on the implemented encoding technique used by data encoder 228 and, accordingly, a myriad of different decoding techniques may be implemented without departing from the invention.

The decoded information is then provided to stimulus output controller and telemetry block 250 (hereinafter "SC&T block 250") that uses the received information to direct the stimulation of the electrodes of electrode array 142. This may include, for example, generating timing and control signals for opening or closing electrode switches 252 for application of stimulus using electrode array 142. A further description of exemplary techniques for opening and closing electrode switches 252 to implement various stimulation schemes is provided U.S. patent application Ser. No. 11/192,014, entitled "Variable Width Electrode Scheme," filed Jul. 29, 2005.

As noted, speech processing unit 126 may also include a speech processor (SP) programming interface 232 through which an audiologist may connect to, for example, modify settings of the speech processing unit 126. For example, SP programming interface 126 may allow an audiologist to connect speech processing unit 126 to a computer or other processor based system. The audiologist may then access speech processing unit 126 via diagnostic and programming user interface software 254 executing on the computer to modify the settings of speech processing unit 126. These settings may be stored, for example, in speech processing (SP) configuration registers 230. For example, the audiologist may use the user interface 254 to modify the mappings of channels to electrodes, including the number and identity of filer channels mapped together, the grouping of electrodes, the stimulation timing, the mode of stimulation, etc. A further description of an exemplary method for an audiologist to modify the mapping of channels and electrodes is provided below.

Filter bank 222, ACS block 224, M&SR block 226, Data encoder formatter 228, SP configuration registers 230 and SP programming interface 232 are described herein as logical blocks of signal processing unit 126 and in practice may be implemented in speech processing unit 116 of FIG. 1 by, for example, software, hardware, or any combination thereof.

Figure 3:
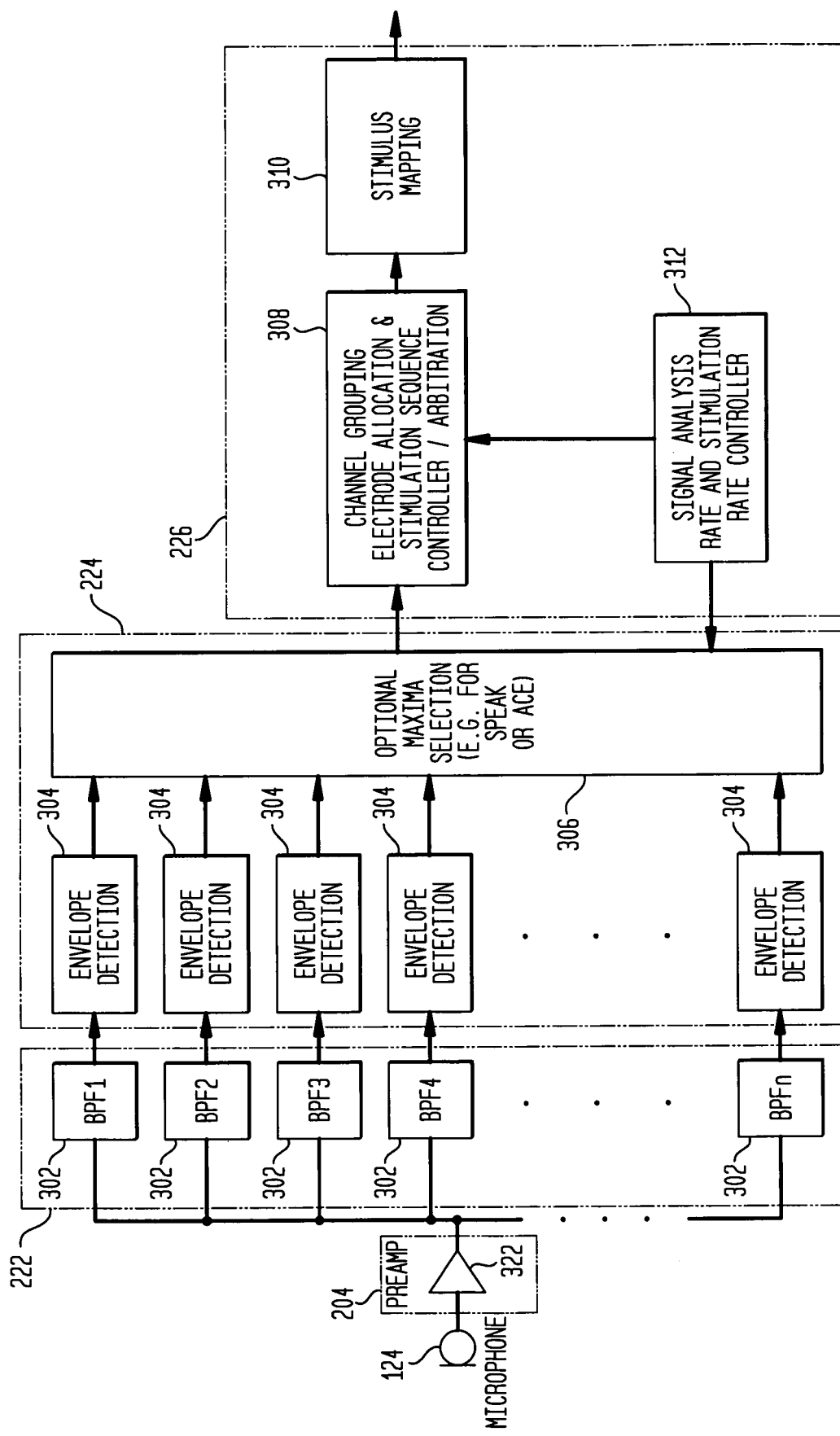
FIG. 3 illustrates a more detailed diagram of logical blocks of FIG. 2.

FIG. 3 illustrates a more detailed diagram of one embodiment of filter bank 222, ASC block 224, and M&SR block 226. As illustrated, microphone 124 may receive analog audio signals that are provided to audio preprocessor 204, that among other things includes a preamplifier 322 for amplifying the signals. Filter bank 222 may include a plurality of band pass filters 302. As discussed above, two principle techniques may be used for implementing filters 302: the SCF technique or the DSP technique. The band pass filtered signals are then provided to ASC block 224, which may include envelope detectors 304 for detecting instantaneous energy estimates (amplitudes) of the signal at the frequency range corresponding to its corresponding band pass filter. ACS block may also optionally include a maxima selector 306 for selecting a number of maxima (i.e., the channels having the largest amplitude). As is well known to those of skill in the art, various techniques may be used for selecting maxima. For example, in systems implementing the Spectral PEAK Extraction (SPEAK) or Advanced Combination Encoders (ACE) speech coding strategies employing an n of m scheme, a fixed number of maxima may be selected from the filter channels, such as for example, the 8, 16, etc. channels with the highest amplitude in a system with, for example, 22 filter channels. Or in other systems, such as a CIS strategy where all filter channels are used for stimulating electrode array 142, a maximal selector 306 need not be used. For simplicity, the embodiments described herein will be described with reference to a system in which maxima selector 306 is not used or turned off when operating in the MEM mode, and all filter channel signals are available for stimulating electrode array 142.

The filter channel signals (or selected maxima) are provided to MS&R block 226. As illustrated, this block may include a channel grouping, electrode allocation and stimulation sequence/arbitration block 308 (hereinafter "CGAS block 308"), a stimulus mapping block 310 (hereinafter, "SM block 310"), and a signal analysis rate and stimulation rate controller 312 (hereinafter "SR block 312")

SR block 312 preferably provides stimulation rate information to CGAS block 308. This stimulation rate information, as discussed above, may be preset by an audiologist. SR block 312 may also provide spectral analysis rate information to ACS block 224. This spectral analysis rate information is used by ACS block 224 to control the rate at which energy estimates of each band are taken by envelope detectors 304 and the rate at which maxima are selected by optional maxima selector 306. Stimulation rates and spectral analysis rates are well known in the art and are not discussed further herein.

CGAS block 308 receives the filter channel signals (or selected maxima) and stimulation rate information and determines the signals for stimulating electrodes of electrode array 142. For example, CGAS block 308 may provide SM block 310 with signals for the rate of stimulation, the group of electrodes to be stimulated, and the current amplitude for stimulating the electrodes. SM block 310 then maps the received information to the electrodes of electrode array 310. This mapping may include amplitude mapping to generate a stimulus current level for each stimulus to be applied along with generating the stimulus pulse timings for generating the pulses in accordance with the implemented strategy (e.g., timing for controlling the pulse widths, the interphase gaps, etc.). This mapping may also include mapping a single filter channel to a single group of one or more electrodes or mapping groups of 2 or more filter channels to a single group of electrodes. In an exemplary embodiment, CGAS block 308 may, for example, provide a group number (e.g., group 8) to SM block 310. SM block 310 then maps this group number (e.g., group number 8) to the electrode(s) belonging to this group (e.g., electrode 4). A further description of mapping a group number to a group of one or more corresponding electrodes is provided below.

Figure 4:
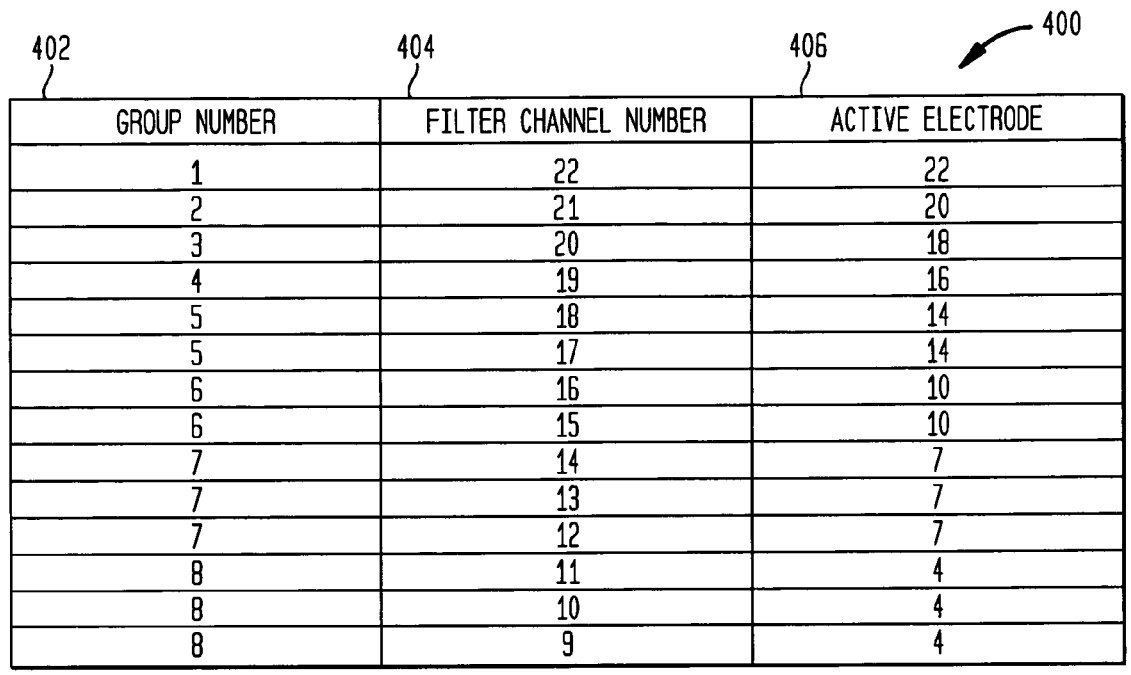
FIG. 4 depicts a table that illustrates an exemplary mapping for implementing an MEM strategy in which multiple filter channels are mapped to a single group of one or more electrodes.

FIG. 4 depicts table 400, which illustrates an exemplary mapping for implementing an MEM strategy in which multiple filter channels are mapped to a single group of one or more electrodes. As shown table 400 includes a Group Number column 402, a Filter Channel Number column 404, and an Active Electrode column 406. The Filter Channel Number column 404 identifies filter channels that are used in this exemplary embodiment. The Active Electrode column 406 identifies the active electrodes that are assigned to the corresponding filter channel listed in Filter Channel Number column 404. As one of ordinary skill in the art is aware, active electrodes are electrodes that are "ON" and available for application of stimulus to an implant recipient. The Group Number column 402 identifies a group to which the filter channel belongs. The group number is used herein for illustrative purposes in describing groups in which multiple filter channels are assigned and in actual implementations a group number need not be used.

As shown in table 400, in this exemplary MEM strategy, there are 8 different groups of filter channels: 4 groups where a single filter channel is mapped to a corresponding single electrode (i.e., groups 1-4); 2 groups where 2 filter channels are mapped to a single electrode (i.e., groups 5 and 6); and 2 groups where 3 filter channels are mapped to a corresponding single electrode (i.e., groups 7 and 8). As such, this strategy will be referred to as a 1:1:1:1:2:2:3:3 strategy. In this example, 14 distinct filter channels are used. This table may be stored in SP configuration registers 230 where it may be modified by an audiologist via SP programming interface 232. Further, this mapping table may also be accessed by CGAS block 308 and SM block 310 to implement the specified MEM strategy. Although table 400 illustrates an example in which filter channels 9-22 are used and there are no gaps between these filter channels, other embodiments are possible where gaps exist. For example, in another embodiment, filter channel 22 may be mapped to electrode 22, filter channel 20 mapped to electrode 20, filter channel 18 mapped to electrode 18, filter channel 16 mapped to electrode 16, filter channels 13-14 mapped to electrode 14, filter channels 10-11 mapped to electrode 10, filter channels 6-8 mapped to electrode 7, and filter channels 2-4 mapped to electrode 4. As with the mapping of table 400, this mapping also provides a 1:1:1:1:2:2:3:3 mapping strategy.

As discussed above, embodiments of the present invention may be used to vary the stimulation rate of signals applied at different frequencies. For example, embodiments may be used in which higher frequency channels are mapped together so that they are stimulated at a higher frequency, as occurs in natural hearing. The following provides a more detailed description of exemplary mechanisms for implementing variable stimulation rates.

In typical systems employing the SPEAK or ACE strategies, the stimulation rate per channel provided by SR block 312 is determined from a preset value stored in SP configuration registers 230. CGAS block 308 then receive the selected maxima and simply cycles through the selected maxima channels providing an electrode number and amplitude value to SM block 310, which then stimulates corresponding electrodes at this fixed stimulation rate. Accordingly, in traditional systems, all electrodes are stimulated at an identical rate. For example, in a traditional system employing an n of m strategy where n=8 and m=22, the system selects 8 maxima from 22 filter channels. Each of these 8 maxima are then applied at the same preset stimulation rate, which may, for example, range from less than 800 pps to greater than 2000 pps.

In an embodiment employing the presently described Multiple Electrode Mapping (MEM) strategy, CGAS block 308 receives the filter channels signals (or selected maxima), and determines the corresponding timing the electrode group corresponding to each received filter channel signal (or maxima) and other signals for stimulating electrodes of electrode array 142. In its simplest form, CGAS block 308 receives the selected maxima and cycles through all channels (in this example, 14 filter channels). FIG. 5 illustrates a table 500, which provides an exemplary stimulus timing sequence for such a simple stimulation strategy. As illustrated, table 500 includes a Channel Group Number column 502 that identifies the channel group by its illustrative number along with the filter channels assigned to this group number. Active Electrode column 504 identifies the active electrodes assigned to the corresponding filter channel group. Stimulus timing sequence columns 506 includes a plurality of time period columns 508. In this example, fourteen filter channels are being used, and as such, fourteen time periods are available for application of stimulus. An X in a particular time period column 508 indicates that, in this example, stimulus for the corresponding filter channels are applied during this time period.

The exemplary MEM strategy of table 500 results in bursts of stimulation on the electrodes to which multiple channels are mapped. For example, if a stimulation rate of 800 pps per channel is used with the 14 different channels of table 500, the total stimulation rate is 11.2 kHz (i.e. 800 Hz/channel*14 channels). Thus, electrode 22, which corresponds to filter channel 22, is stimulated at a rate of 800 Hz (i.e., it is stimulated once per frame of 14 pulses). Electrode 4, which is mapped in this example to channel group 8 that includes 3 filter channels (filter channels 2, 3, and 4), is stimulated 3 consecutive times (i.e., at times t1, t2, and t3) and then not stimulated again until the timing sequence is repeated. Thus, electrode 4 is stimulated 3 times per 14 pulses, for an effective stimulation rate of 2400 Hz (3*800 Hz). This strategy, however, results in much higher burst rate for such a 3-channel to 1 electrode allocation. That is, in this example, each pulse has a pulse duration of 89 microseconds (1/11.2 kHz). Thus, electrode 4 is stimulated a total of 3 times over a duration of 267 microsecond (3*89 microseconds), or at a burst stimulation rate of 11.2 kHz (i.e., the total stimulation rate). Such a strategy may be acceptable for relatively low stimulation rates of 800 pps or less.

For embodiments using a higher stimulation rate (e.g., of >2000 pps), the burst rate for the same situation (i.e., a 3-1 mapping) would be >6000 pps. In such examples, it may be desirable to limit the maximum burst frequency to control temporal integration effects, in which case the Stimulation Sequence Control function would cause all multiple channel electrodes to be sequenced with all other electrodes to spread out the stimuli that would otherwise be delivered as contiguous burst. FIG. 6 illustrates table 600, which provides such an alternative channel timing sequence.

As shown in the exemplary timing sequence of table 600, electrode 4 (mapped to channel group 8) is still stimulated at 3 times the stimulation rate of 800 pps (i.e., it is stimulated at an effective stimulation rate of 2.4 kHz). But instead of channel 4 being stimulated 3 consecutive times and having a burst rate equal to the total stimulation rate (11.2 kHz), the stimulation of electrode 4 is spread out over a longer time period. For example, in this embodiment, electrode 4 is stimulated 3 times over a period of 11 pulses, where each pulse is 89 microseconds, for a total period of 981 microseconds. Thus, in this example, electrode 4 is stimulated at a burst rate of 3054 Hz (3 pulses/981 microseconds). These tables present exemplary mechanisms that CGAS block 308 may utilize to stimulate electrodes according to the exemplary MEM strategy being discussed. It should be noted that numerous other strategies may be implemented for stimulating electrodes of electrode array 142 without departing from the invention. As will be discussed in further detail below, the mapping of filter channels to electrodes and the timing strategy for stimulating the electrodes may be set and modified by an audiologist using an external computer connected to the speech processing unit 126 via SP programming interface 232.

In addition to be useful in enabling different frequency channels to be stimulated at different channel rates, embodiments of the MEM strategy may be used to reduce the number of effective filter channels and/or to effectively modify the filter channels bandwidth. For example, if multiple filter channels are mapped to a single group of one or more electrodes, this has the effect of combining the multiple filter channels into a single wider bandwidth filter channel that is stimulated at a higher stimulation rate. As such, the MEM strategy may be used to convert a system with a large number of filter channels that provide high spectral selectivity and a predefined temporal resolution (determined by the available stimulation rate per channel) to a system with a smaller number of filter channels that provide reduced spectral resolution, but a greater temporal resolution via higher stimulation rates to the combined high frequency channels (in proportion to the number of channels that are combined. As discussed above, higher temporal resolution in the high frequency channels has been shown to improve speech recognition.

Figure 7:
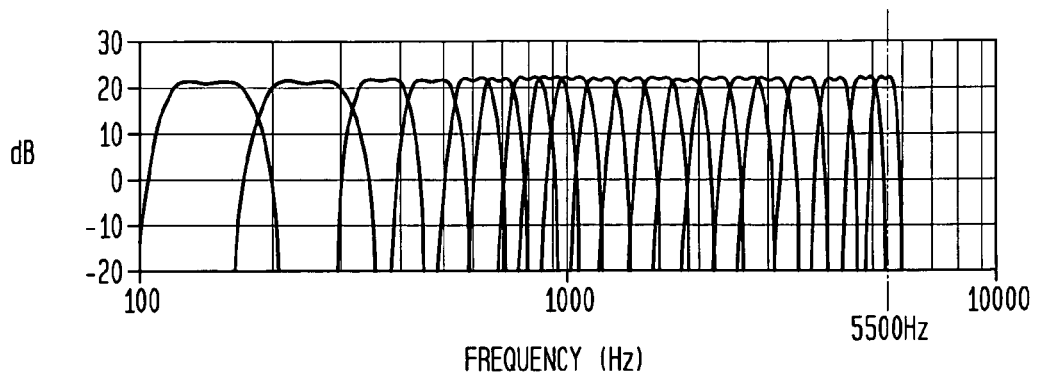
FIG. 7 illustrates filter bands for an exemplary SCF band pass filter bank
Figure 8A:
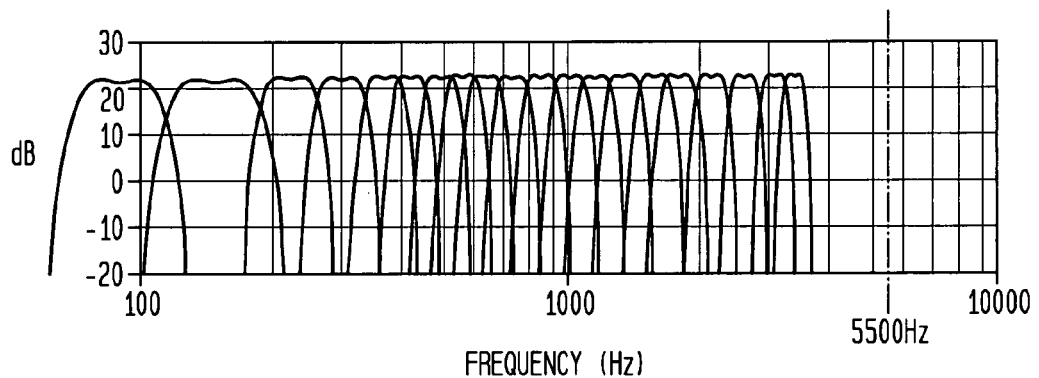
FIG. 8A illustrates exemplary filter bands for the SCF band pass bank of FIG. 7, where the filter clock frequency has been decreased.
Figure 8B:
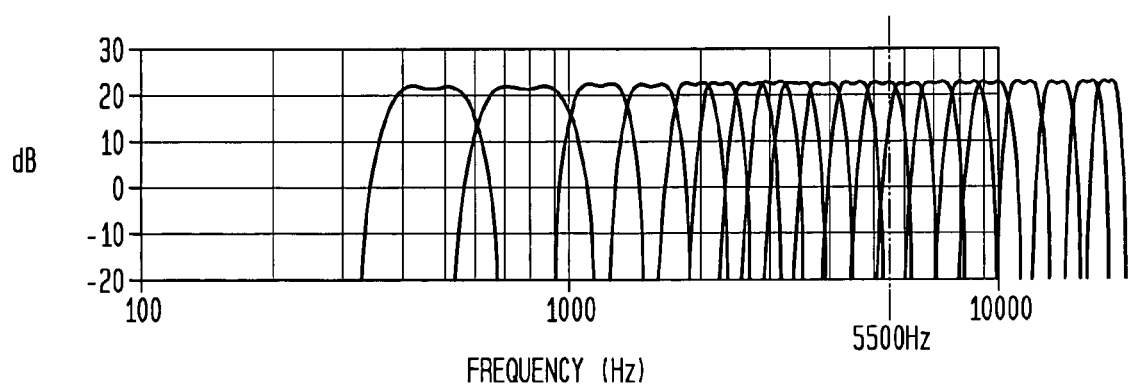
FIG. 8B illustrates exemplary filter bands for the SCF band pass filter bank of FIG. 7, where the filter clock frequency has been increased.

As discussed above, band pass filter bank 222 is typically implemented via either the SCF or DSP technologies. When using the SCF technology, the centre frequencies of the SCF filters can be shifted up or down by changing the filter clock frequency. This has the effect of decreasing or increasing the useful audio frequency range (approximately 100 Hz to 5,500 Hz) covered by the SCF band pass filters. FIG. 7 illustrates filter bands for an exemplary SCF band pass filter bank. As shown, this SCF filter bank has 20 bands in the 100 to 5,500 Hz range. These center frequency of these filter bands may then be increased or decreased by adjusting the filter clock frequency. For example, FIG. 8A depicts the effect of decreasing the filter clock frequency, which is to shift the center frequency of the filters down, resulting in the same number of channels covering a lower range of frequencies. The center frequency of the filter bands may also be increased by, for example, increasing the filter clock frequency. Shifting the filter clock frequency may also be used to reduce the number of filter channels in the useful audio frequency range. FIG. 8B illustrates exemplary filter bands for the SCF band pass filter bank of FIG. 7, where the filter clock frequency has been increased. As illustrated, FIG. 8A describes 12 bands in the 100 Hz to 5,500 Hz range. However, using such a system may result in the band pass filters being shifted too high and low frequency information being lost. For example, as shown if FIG. 8A, this system results in low frequency information below 800 Hz being lost. This may not be desirable. An MEM strategy, such as described above, offers an improved way to achieve a desired number of effective filter channels while still being able to take advantage of the lower power consumption SCF technology. By using the MEM technology, multiple filter channels may be combined to achieve any desired number of effective filter channels while not losing low frequency information and As discussed above, an audiologist may access the speech processor 126 to modify its settings via SP programming interface 232. The following provides a more detailed explanation of two exemplary methods that may be used for modifying the settings for a speech processing unit 126. Although two exemplary methods are provided below, it should be noted that other methods may be used without departing from the invention.

Figure 9:
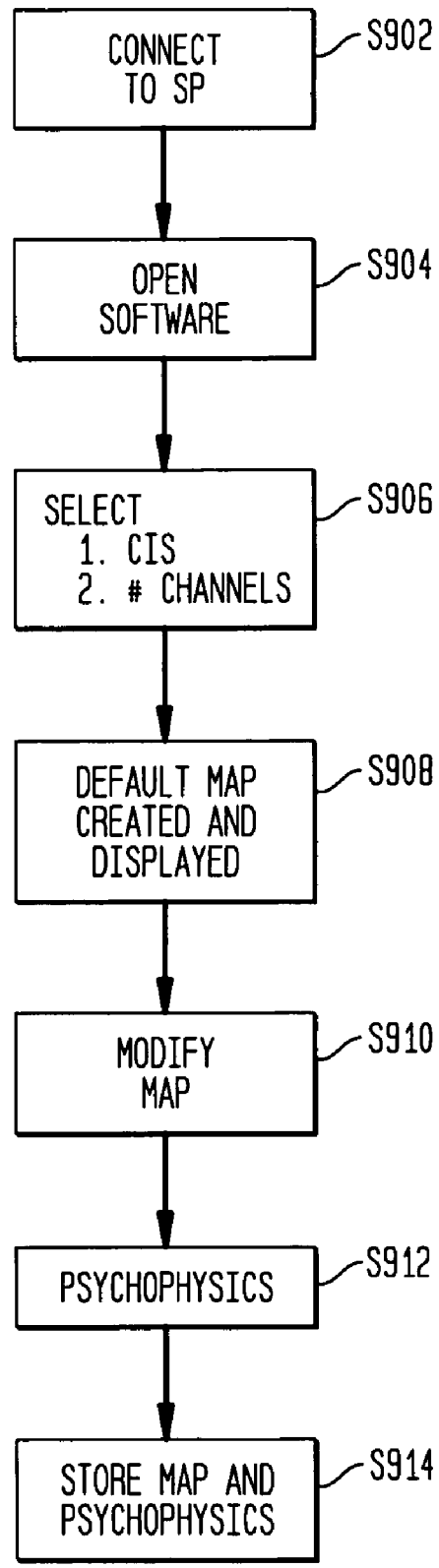
FIG. 9 illustrates an exemplary flow diagram for specifying settings to implement an MEM strategy in a speech processing unit.

FIG. 9 illustrates an exemplary flow diagram for specifying settings to implement an MEM strategy in a speech processing unit. Initially, an audiologist connects a computer or other device to speech processing unit 126 (S902). This may be achieved by, for example, connecting a cable from the computer to the SP programming interface 232. The audiologist may then open a Diagnostic and Programming User Interface software program, such as program 254, that provides a user interface for modifying the settings of speech processing unit 126 (S904). Additionally, this software may communicate with speech processing unit 126 to initially obtain information regarding the speech processing unit such as, for example, the number of filters channels of filter bank 222, the number of electrodes of electrode array 142, etc.

Using the user interface, the audiologist may then select the desired speech coding strategy (e.g., CIS, ACE, SPEAK) and the desired number of effective filter channels (S906). In this example, bandpass filters 222 will be described as having 22 filter channels, electrode array 142 has 22 electrodes, and the user selects the CIS strategy and 12 effective filter channels. Using this information, the software then creates a default channel map that it then presents to the audiologist (S908). This default map may be, for example, a 22 channel map with 10 of the 22 channels disabled (i.e., unused) and 12 of the channels mapped to a corresponding single electrode in a 1:1 correspondence. This may be accomplished, by for example, using an SCF scheme, such as illustrated in FIG. 8B. FIG. 10 illustrates table 1000, which provides an exemplary table of a default mapping that provides 12 effective filter channels. As illustrated, table 1000 includes a Filter Channel Number column 1002, a used/unused column 1004, an Electrode column 1006, and an Active/inactive column 1008. The Used/Unused column 1004 indicates whether the corresponding filter channel is being used in this scheme, where a "1" indicates it is in use, and a "0" indicates that it is not used. The Active/Inactive column 1008 indicates whether the corresponding electrode identified in electrode column 1006 is active or inactive (i.e., is to be used or not), where "1" indicates that the electrode is active and "0" indicates that it is inactive. Arrows 1010 are used to illustrate the mapping of filter channels to electrodes. For example, as shown, filter channel 22 is mapped to electrode 22, filter channel 21 is mapped to electrode 21, filter channel 20 is mapped to electrode 19, filter channel 19 is mapped to electrode 18, filter channel 18 is mapped to electrode 16, filter channel 17 is mapped to electrode 14, filter channel 16 is mapped to electrode 12, filter channel 15 is mapped to electrode 10, filter channel 14 is mapped to electrode 8, filter channel 13 is mapped to electrode 6, filter channel 12 is mapped to electrode 4, and filter channel 11 is mapped to electrode 2. In an alternative embodiment, the 12 selected channels may be evenly spaced over the 22 filter channels using, for example, a band pass filter scheme such as illustrated in FIG. 7. For example, in such an alternative embodiment, filter channels, 22, 20, 18, 16, 14, 12, 10, 8, 6, 4, 2, and 1 may be used where each is mapped to a single corresponding electrode in a 1:1 fashion (i.e., the filter channels are mapped to electrodes 22, 20, 18, 16, 14, 12, 10, 8, 6, 4, 2, and 1, respectively).

This default table may then be modified by the audiologist (S910). This may be accomplished by the audiologist, for example, clicking on the entries they wish to modify and manually modifying the entries. For example, the audiologist may click on a filter channel that brings up a window that allows the audiologist to specify to which electrode the filter channel is mapped. It should be noted that this is but one example and numerous mechanisms are possible for permitting an audiologist to specify mappings without departing from the invention. Additionally, the software may include a validation function to ensure that the audiologist's entries are correct and notify the audiologist of any incorrect entries, thus allowing the audiologist to correct any such errors.

FIG. 11 illustrates table 1100, which provides an exemplary table of a mapping after modification by an audiologist of the mapping of table 1000 that provides 12 effective filter channels mapped to 8 electrodes. Circles 1112 indicate the groupings of filter channels. This mapping includes mappings of multiple filter channels to a single group of one or more electrodes. For example, as illustrated filter channel 22 is mapped to electrode 22, filter channel 21 is mapped to electrode 20, filter channel 20 is mapped to electrode 18, filter channel 19 is mapped to electrode 16, filter channel 18 is mapped to electrode 14, filter channels 16 and 17 are mapped to electrode 10, filter channels 14 and 15 are mapped to electrode 7 and filter channels 11, 12, and 13 are mapped to electrode 4. Although in this example, all used filter channels are adjacent, in other examples they need not be adjacent and gaps may exist between used filter channels.

This exemplary mapping strategy maps 12 filter channels to 8 different electrodes in a 1:1:1:1:1:2:2:3 manner (i.e., 5 groups where 1 filter channel is mapped to 1 electrode; 2 groups where 2 filter channels are mapped to 1 electrode, and 1 group where 3 electrodes are mapped to a single electrode). In an alternative embodiment, such as the alternative to table 1000 discussed above, the audiologist may specify a mapping scheme in which gaps in the filter channels exist. For example, the audiologist may specify a mapping scheme in which filter channel 22 is mapped to electrode 22, filter channel 19 is mapped to electrode 19, filter channel 16 is mapped to electrode 16, filter channel 14 is mapped to electrode 14, filter channel 12 is mapped to electrode 12, filter channels 9 and 10 are mapped to electrode 10, filter channels 6 and 7 are mapped to electrode 7, and filter channels 2,3, and 4 are mapped to electrode 4.

After the audiologist modifies the mappings, the audiologist may then perform psychophysics on the selected electrodes to determine the threshold and maximum comfort levels for each of the selected electrodes (S912). This information may then be stored in SP configuration registers 230 for use by the signal processing unit (S914). It should be noted that table 1100 provides one exemplary mapping and other mappings may be used, such as the mapping illustrated in table 400, without departing from the invention.

Figure 12:
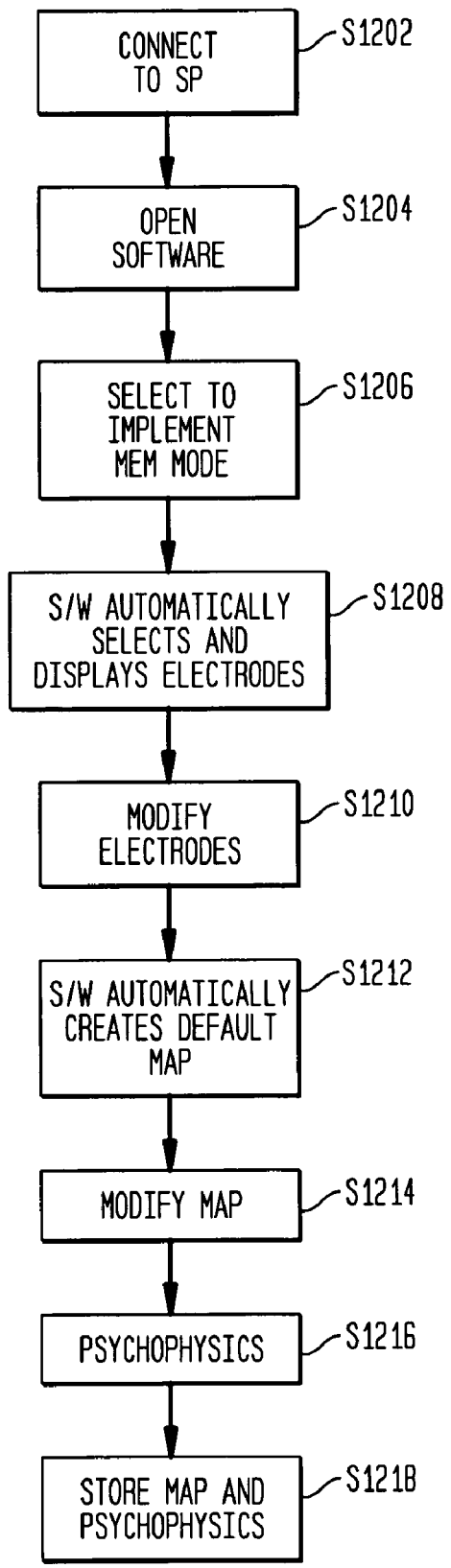
FIG. 12 provides an alternative exemplary flow diagram for specifying the settings of a speech processing unit.

FIG. 12 provides an alternative exemplary flow diagram for specifying the settings of a speech processing unit. As with the flow of FIG. 9, the audiologist first connects a computer, or other device, to the speech processing unit 126 (S1202) and opens Diagnostic and Programming user interface software 254 for modifying the settings of the speech processing unit 126 (S1204). The audiologist may then select to implement an MEM strategy (S1206). For example, an audiologist may click on a "Multiratio CIS" icon displayed in a user interface to begin implementing an MEM strategy, may click on an appropriate toolbar, or may select to implement the MEM strategy by any other appropriate means. The audiologist may then be prompted to enter the number of electrodes they desire to set as active (e.g., 12) along with the total desired frequency range for the filter bank 222 (e.g., 800 Hz to 10 kHz). The software may then automatically select the electrodes to use and display the selected electrodes to the user (S1208). This default selection of electrodes may, for example, be such that the selected electrodes are evenly spaced across the selected frequency range, such as the selected electrodes illustrated in table 1000.

The audiologist may then modify the selected electrodes (S1210). This may be accomplished by the audiologist clicking on the entries in a displayed table and manually selecting electrodes as either active or inactive. Once the electrodes are selected, the software may then automatically allocate stimulation rate integer ratios for each electrode based on default lookup tables that may be stored by the software and modifiable by the audiologist (S1212). For example, this default lookup table may store information indicating higher frequency electrodes are to be stimulated at a higher rate than lower frequency electrodes. For example, the table may store integer values indicating that high frequency electrodes are to be stimulated at a rate three times greater than low frequency electrodes, and mid frequency electrodes are to be stimulated at a rate twice that of low frequency electrodes. These selected stimulation rate ratios are then used by the software to determine the number of filter channels to be mapped to each of the selected electrodes. For example, a given map may use ratios of 1:1:1:1:2:2:3:3, such as the map of table 400 or, for example, ratios of 1:1:1:1:1:2:2:3, such as the map of table 1100. These ratios may be stored in the default look up tables. Additionally, the software may also automatically divide the frequency range among the channels using, for example, default look up tables.

The selected mapping table may then be presented to the audiologist, who may manually modify the settings if desired (S1214). After which, the audiologist may then perform standard psychophysics on the selected electrode to set the threshold and maximum comfort level of each of the selected electrodes (S1216). This information may then be stored in SP configuration registers 230 for use by the speech processing unit 126 (S1218).

Further, in addition to specifying the mapping of the filter channels to electrodes, the software may also permit the audiologist to specify the strategy for stimulating the electrodes. For example, the audiologist may be presented with a default stimulation strategy, such as illustrated in Tables 500 and/or 600. The user may then select to manually modify the table to effect a different stimulation strategy. Additionally, the software may permit the audiologist to enter parameters that the software will use in creating the default stimulation strategy. For example, the audiologist may be able to specify that the maximum burst rate for any particular mapping not exceed a particular value, such as, for example, 4000 Hz or a fraction of the total stimulation rate (e.g., $\frac{1}{8}^{th}$ the total stimulation rate or 2700 Hz for a system with a total stimulation rate of 21.6 kHz). Or, for example, the software may by default generate a stimulation strategy that minimizes the maximum burst rate as much as possible. The software may also permit the audiologist to specify other settings for use by the system, such as the stimulation rate for each channel (e.g., 800 pps), the spectral analysis rate, etc.

Although the above-discussed embodiments were discussed with reference to the CIS speech encoding strategy, other speech coding strategies may be used when converting sound into an electrical stimulation signals. For example, embodiments of the present invention may be used in combination with a variety of speech strategies including but not limited to Continuous Interleaved Sampling (CIS), Spectral PEAK Extraction (SPEAK), Advanced Combination Encoders (ACE), Simultaneous Analog Stimulation (SAS), MPS, Paired Pulsatile Sampler (PPS), Quadruple Pulsatile Sampler (QPS), Hybrid Analog Pulsatile (HAPs), n-of-m and HiReS™, developed by Advanced Bionics. SPEAK is a low rate strategy that may operate within the 250-500 Hz range. ACE is a combination of CIS and SPEAK. Examples of such speech strategies are described in U.S. Pat. No. 5,271,397, the entire contents and disclosures of which is hereby incorporated by reference. The present invention may also be used with other speech coding strategies, such as a low rate strategy called Spread of Excitation which is described in U.S. Provisional No. 60/557,675 entitled, "Spread Excitation and MP3 coding Number from Compass UE" filed on Mar. 31, 2004, U.S. Provisional No. 60/616,216 entitled, "Spread of Excitation And Compressed Audible Speech Coding" filed on Oct. 7, 2004, and PCT Application WO 02/17679A1, entitled "Power Efficient Electrical Stimulation," which are hereby incorporated by reference herein.

Further, although the above-discussed embodiment were discussed with reference to mapping groups of filter channels to a single electrode, in other embodiments electrodes may be electrically coupled to form an electrode group comprising two or more electrodes. For example, in an embodiment any desired combination of two-or more electrodes may be electrically-coupled to each other so that a stimulating signal may be simultaneously applied to or generated on (generally referred to as "applied to") the electrically coupled electrodes via a single source, such as a single current source. When implemented in a prosthetic hearing implant system, the group(s) of electrically-coupled electrodes may each be managed as a single electrodes along with any individual electrodes. That is, the electrode groups and single electrodes may be controlled to simultaneously or sequentially apply stimulating signal to the cochler in accordance with a selected stimulation strategy.

Altering the electrode geometry by electrically coupling electrodes provides many advantages. Take, for example, systems in which the electrodes are arranged in a linear array, as is commonly utilized in a prosthetic hearing implant. Electrically coupling and/or de-coupling two or more adjacent or proximate electrodes of the array changes the effective electrode surface area through which a stimulating signal is applied to the auditory nerves of a cochlear. Adjusting the effective width of electrodes allows for the dynamic control of the spread of excitation by altering the region of neural excitation. In addition, the effective electrode width may be adjusted to adapt the electrode array to a cochlea having a particular pattern of functional auditory nerves.

A further advantage in the above or other applications is that electrically coupling two or more electrodes reduces electrode impedance. Because power consumption typically increases with increasing stimulus current, a reduction in electrode impedance reduces the power consumption of the implant system. This is particularly advantageous when used in conjunction with high-density electrode arrays. The design of intra-cochlea electrode arrays has been driven by the need to achieve a higher density of discrete electrodes positioned closer to the inner wall of the cochlea (or modiolus) with the objective of increasing spectral resolution and reducing stimulation thresholds. As the density of an electrode array increases (density being defined by the number of electrodes per unit length of the array), the electrode area becomes smaller, resulting in an increased impedance. By electrically coupling two or more electrodes, the impedance of the electrode array may be reduced. A further description of methods and systems for electrically-coupling electrodes to form groups of electrodes is provided in the above-incorporated by reference U.S. patent application Ser. No. 11/192,014, entitled "Variable Width Electrode Scheme," filed Jul. 29, 2005.

Figure 13:
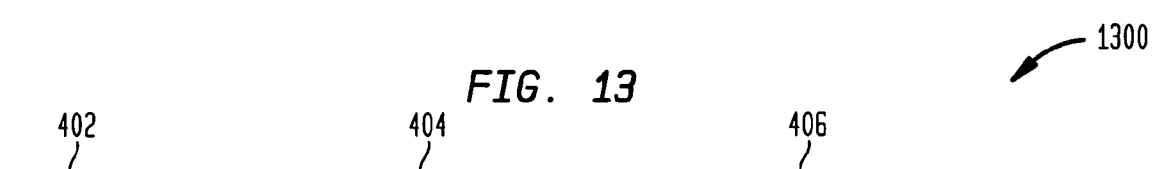
FIG. 13 illustrates an exemplary mapping that includes mappings of multiple channels to groups of two or more electrically-coupled electrodes.

FIG. 13 illustrates table 1300, which provides an exemplary mapping that includes mappings of multiple channels to groups of two or more electrically-coupled electrodes. For example, as shown, group 1 consisting of filter channel 22 is mapped to three electrodes (electrodes 20, 21, and 22), group 2 consisting of filter channel 19 is mapped to electrodes 18 and 19, group 3 consisting of filter channel 15 is mapped to electrodes 15, 16, and 17, group 4 consisting of electrode 14 is mapped to electrode 14, group 5 consisting of filter channels 12 and 13 is mapped to electrodes 12 and 13, group 6 consisting of filter channels 10 and 11 is mapped to electrode 10, group 7 consisting of filter channels 6, 7, and 8 is mapped to electrode 7, and group 8 consisting of filter channels 2, 3, and 4 is mapped to electrodes 3 and 4.

It should be noted that table 1300 merely illustrates on exemplary way in which multiple filter channels may be mapped to groups of one or more electrodes. For example, in table 1300, there are gaps between filter channels (e.g., filter channel 21 is not used). In other embodiments, it may not be desirable to have gaps. In such an example, adjacent filter channels may be used and a scheme such as illustrated in FIG.

8B may be used to reduce the number of used filter channels. Numerous other mappings are possible without departing from the invention.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All documents, patents, journal articles and other materials cited in the present application are hereby incorporated by reference. Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for delivering a stimulating signal by a stimulating medical device having a plurality of electrodes, comprising:
   receiving a signal;
   filtering the received signal to obtain a plurality of band pass filtered signals;
   delivering to each electrode of a first group of one or more electrodes, a first set of stimulation signals, wherein the first set of stimulation signals comprises stimulation signals for each of a first filter channel group of two or more band pass filtered signals; and
   delivering to each of electrodes of a second group of one or more electrodes, a second set of stimulation signals, wherein the second set of stimulation signals comprises stimulations signals for each of a second filter channel group of one or more band pass filtered signals; and
   wherein the first set of stimulation signals are delivered at a different effective stimulation rate than the second set of stimulation signals.

2. The method of claim 1, wherein the band pass filtered signals of the first filter channel group comprise higher frequency signals than the band pass filtered signals of the second filter channel group; and wherein the first set of stimulation signals are delivered at a higher effective stimulation rate than the second set of stimulation signals.

3. The method of claim 2, wherein the first filter channel group are mapped to a first group of one or more electrodes and the second filter channel group are mapped to a second group of one or more electrodes, and wherein the mapping is performed by software that automatically maps higher frequency filter channel groups to more band pass filters than lower frequency channel groups.

4. The method of claim 1, wherein the delivering of the first set of stimulation signals, comprises delivering the signals of the first set of stimulation signals interspaced with other stimulation signals in order to reduce a burst rate for the delivering of the first set of stimulation signals.

5. The method of claim 4, wherein the delivering of the first set of stimulation signals comprises automatically limiting the burst rate for delivering the first set of stimulation signals.

6. The method of claim 1, wherein the first group of electrodes comprises two or more electrodes, the method further comprising:
   electrically coupling the electrodes comprising the first group of electrodes; and
   wherein the delivering of the first set of stimulation signals comprises simultaneously delivering to the group of electrically-coupled electrodes a stimulation signal from the first set of stimulations signals.

7. The method of claim 6, wherein the simultaneous delivering of the stimulation signal to the first group of electrodes comprises:
   simultaneously delivering the stimulation signal to the first group of electrically-coupled electrodes a stimulation signal via a single current source.

8. A cochlear implant system, comprising:
   a plurality of electrodes disposed in a cochlear of a recipient, wherein the plurality of electrodes comprise a first group of one or more electrodes and a second group of one or more electrodes;
   a speech processing unit comprising a plurality of band pass filters configured to process received acoustical signals to obtain a plurality of band pass filtered signals; and
   a stimulator unit configured to deliver to each electrode of a first group of one or more electrodes, a first set of stimulation signals, wherein the first set of stimulation signals comprises stimulation signals for each of a first filter channel group of two or more band pass filtered signals, and to deliver to a second group of one or more electrodes a second set of stimulation signals, wherein the second set of stimulation signals comprises stimulations signals for each of a second group of one or more band pass filtered signals, and wherein the first set of stimulation signals are delivered at a different effective stimulation rate than the second filter channel set of stimulation signals.

9. The system of claim 8, wherein the speech processing unit further comprises:
   a processor configured to map the first filter channel group of two or more band pass filtered signals to the first group of one or more electrodes, and to map the second filter channel group of one or more of the band pass filtered signals to the second group of one or more electrodes; and
   wherein the band pass filtered signals of the first filter channel group comprise higher frequency signals than the band pass filtered signals of the second filter channel group; and
   wherein the first set of stimulation signals are delivered at a higher effective stimulation rate than the second set of stimulation signals.

10. The system of claim 9, wherein the processor comprises software configured to map the first filter channel group to the first group of one or more electrodes and map the second filter channel group to the second group of one or more electrodes, and wherein the software automatically maps higher frequency filter channel groups to more band pass filters than lower frequency channel groups.

11. The system of claim 8, wherein the speech processing unit is configured to direct the stimulator unit to deliver the signals of the first set of stimulation signals interspaced with other stimulation signals in order to reduce a burst rate for the delivering of the first set of stimulation signals.

12. The system of claim 11 wherein the speech processing unit comprises software configured to automatically limit the burst rate for delivering the first set of stimulation signals.

13. The system of claim 8, wherein the first group of electrodes comprises two or more electrodes, and wherein the stimulator unit is configured to electrically couple the electrodes comprising the first group of electrodes, and to simultaneously deliver a stimulation signal to the first group of electrically-coupled electrodes.

14. The system of claim 13, wherein the stimulator unit is further configured to simultaneously deliver the stimulation signal to the first group of electrically-coupled electrodes via a single current source.

15. A system for delivering a stimulating signal by a stimulating medical device having a plurality of electrodes, comprising:

means for receiving a signal;

means for filtering the received signal to obtain a plurality of band pass filtered signals;

means for delivering to each electrode of a first group of one or more electrodes, a first set of stimulation signals, wherein the first set of stimulation signals comprises stimulation signals for each of a first filter channel group of two or more band pass filtered signals; and means for delivering to each of electrodes of a second group of one or more electrodes, a second set of stimulation signals, wherein the second set of stimulation signals comprises stimulations signals for each of a second filter channel group of one or more band pass filtered signals; and wherein the first set of stimulation signals are delivered at a different effective stimulation rate than the second set of stimulation signals.

16. The system of claim 15, wherein the band pass filtered signals of the first filter channel group comprise higher frequency signals than the band pass filtered signals of the second filter channel group; and wherein the first set of stimulation signals are delivered at a higher effective stimulation rate than the second set of stimulation signals.

17. The system of claim 16, wherein the first filter channel group are mapped to a first group of one or more electrodes and the second filter channel group are mapped to a second group of one or more electrodes, and wherein the mapping is performed by software that automatically maps higher frequency filter channel groups to more band pass filters than lower frequency channel groups.

18. The system of claim 15, wherein the first group of electrodes comprises two or more electrodes, the system further comprising:

means for electrically coupling the electrodes comprising the first group of electrodes; and wherein the means for delivering of the first set of stimulation signals comprises means for simultaneously delivering to the group of electrically-coupled electrodes a stimulation signal from the first set of stimulation signals.

* * * * *